United States Patent [19]

Ewing et al.

[11] Patent Number: 5,624,539
[45] Date of Patent: Apr. 29, 1997

[54] REAL TIME MONITORING OF ELECTROOSMOTIC FLOW IN CAPILLARY ELECTROPHORESIS

[75] Inventors: Andrew G. Ewing, State College, Pa.; Mark A. Hayes, Riverside, Calif.

[73] Assignee: The Penn State Research Foundation, University Park, Pa.

[21] Appl. No.: 491,649

[22] Filed: Jun. 19, 1995

[51] Int. Cl.$^6$ .................................................. G01N 27/26
[52] U.S. Cl. ........................ 204/451; 204/454; 204/600; 204/601
[58] Field of Search ............... 204/299 R, 180.5, 204/180.1, 183.3, 451, 454, 600, 601

[56] References Cited

U.S. PATENT DOCUMENTS

| | | | |
|---|---|---|---|
| 3,454,487 | 7/1969 | Riddick | 204/299 R |
| 4,433,299 | 2/1984 | Kawai et al. | 324/464 |
| 5,009,760 | 4/1991 | Zare et al. | 204/453 |
| 5,022,972 | 6/1991 | Dávid et al. | 204/183.3 |
| 5,092,972 | 3/1992 | Ghowsi | 204/454 |
| 5,180,475 | 1/1993 | Young et al. | 204/454 |
| 5,240,585 | 8/1993 | Young et al. | 204/601 |

OTHER PUBLICATIONS

M. Miyamoto et al. (Electro–osmotic Flow Measurements, Journal of Membrane Science, 41 (1989) 377–391) No month available.

Van De Goor, et al., Journal of Chromatography, 470 (1989) 95–104.

E. Delatour, et al. Apparatus for Alternating Field Microelectrophoresis, Rev. Sci. Instrum., vol. 47, No. 12, Dec. 1976, 1531–1535.

*Primary Examiner*—Kathryn L. Gorgos
*Assistant Examiner*—Alex Noguerola
*Attorney, Agent, or Firm*—Thomas J. Monahan

[57] ABSTRACT

An electrophoretic separation apparatus includes a capillary tube having a length, a cross section, an inlet and an outlet. A first reservoir containing a solvent and, upon injection, a solute is in fluid-flow communication with the inlet and a second reservoir containing at least a solvent is also in fluid flow communication with the outlet, the capillary thereby being filled at least with the solvent. A first power supply applies a direct voltage separation potential between the first and second reservoirs and along the length of the capillary to thereby establish an electrophoretic flow of the solute therethrough. A second power supply applies an alternating voltage upon the direct voltage, and the DC impedance and AC impedance values are determined and subtracted to provide a direct measurement of the electroosmotic flow.

2 Claims, 4 Drawing Sheets

REAL TIME MONITORING OF ELECTROOSMOTIC FLOW IN CAPILLARY ELECTROPHORESIS

FIELD OF THE INVENTION

This invention relates to capillary electrophoresis instruments and, more particularly, to an improved system for the real time monitoring of electroosmotic flow velocities in a capillary electrophoresis instrument. An objective of the invention is to combine the electronic control of electroosmotic flow to better control flow in a capillary electrophoresis instrument.

BACKGROUND OF THE INVENTION

Zone electrophoresis in capillaries is widely used to accomplish liquid-phase separations of various solutes. Capillary electrophoresis has been used for separation of small and large molecules, various amino acids, alkylamines and various proteins. In brief, a capillary zone electrophoresis device includes a buffer-filled capillary tube that is placed between two buffer reservoirs. A potential field is applied across the length of the capillary tube, and then ionic solutes in one buffer reservoir differentially migrate through the capillary into the other reservoir. Small diameter silica based tubes are employed as the capillaries in capillary zone electrophoresis (CZE) instruments.

A distinguishing property of the capillary electrophoresis instrument is electroosmotic flow. Immediately adjacent to the solid-liquid interface at the interior of the silica-based capillary wall, a stagnant double layer of solute/solvent is found. Under normal aqueous conditions, the silica capillary wall surface has an excess of charge resulting from an ionization of surface functional groups. Thus, SiOH groups are ionized leaving SiO— at the wall surface and H+ ions in the solution and in the stagnant double layer adjacent to the capillary wall. This action creates a potential across these layers, part of which is termed the zeta potential. The zeta potential is dependent upon the viscosity of the fluid, the dielectric constant of the solution and the charge on the inner surface of the wall of the capillary. The cationic counter ions ($H_3O+$, $Na+$ typically) in the diffuse solvent/solute layer migrate towards the cathode and because these ions are solvated, they drag solvent with them. The extent of the potential drop across the double layer governs the rate of flow. It is known that control of electroosmotic flow is effective in improving electrophoretic resolution and efficiency and is a controlling factor in obtaining reproducible results in a CZE apparatus.

DISCUSSION OF THE PRIOR ART

The prior art discloses a number of ways to alter electroosmotic flow, including derivatizing the inner surfaces of a capillary by coating them with a monomolecular layer of non-cross-linked polyacrylamide, which discourages the osmotic effect and adsorption of solutes onto the inside of the capillary. Also, electroosmotic flow may be altered by altering the buffer pH, the concentration of the buffer, the addition of surface-active species such as surfactants, glycerol, etc., or various organic modifiers to the buffer solution.

Is known that the conductivity of a solution due to ion mobility and the flux of ions due to bulk buffer movement may be measured independently. The real-time monitoring of electroosmotic flow has been the subject of many studies. An excellent summary of work prior to 1989 is contained in an article by van de Goor et al. (J. Chromatogr.470(1989) pp. 95). A brief description of the various methods is provided below to facilitate a complete discussion between the present work and those prior to it.

The first and most commonly applied of these methods is the use of a neutral marker. Neutral species are swept along at the electroosmotic flow rate (in the absence of surface interactions). Therefore if the length from the injector to the detector is known, the flow may be calculated from the elution time. This is limited because it is a batch process and only represents the average flow during the time it takes for the neutral marker to elute. Colloidal particles of the same material as that of the capillary have also been used. This method suffers from large differences in the measurement system and the separative system and certainly would be problematic in coated capillaries where the surface chemistry is poorly characterized.

Streaming potentials have also been used to determine the zeta potential and the flow is calculated from this value. This system requires pressure driven buffer reservoirs and highly sensitive voltage sensing devices. This also requires off-line analysis from which the flow is back-calculated.

Another method to directly measure electroosmotic flow is to weigh the mass transferred from the injection or that delivered to the detection reservoir. This of course requires calibration for each buffer system and the high accuracy mass balance system.

Monitoring the current flow in a capillary has been used to examine the rate of electroosmotic flow when a buffer of differing concentration is introduced into the injection end of the capillary. Under these conditions the total conductivity across the capillary is proportional to a weighted average of the conductivity of each buffer solution. Therefore, the rate of change in the current is a function of the electroosmotic flow. This method suffers from two major problems. Since it is a batch process the buffer must be changed and flow will differ slightly in each of the buffer-filled sections. Reference is made to U.S. Pat. No. 5,009,760 which discloses a process which requires changing buffers, and which is not a real-time monitoring process since the buffer must migrate the entire length of the capillary.

Two real-time monitoring systems have recently been proposed. The first is a conductivity flow-monitoring device placed at the detection-end of the capillary. This system is based on the ionic strength of the buffer reservoir changing with the delivery of a more concentrated buffer from within the capillary. The other system is a laser-induced florescence post-column reaction system in which the fluorescent signal is proportional to the flow. Both of these designs suffer from engineering and manufacturing complexities, and also preclude the use of post-column detectors such as electrochemical and mass spectrometric detectors.

Reference is also made to U.S. Pat. 5,092,972 in which a second electric potential is applied between the capillary walls and the liquid to change the charge on the wall and thus allow manipulation of the zeta potential and thereby change the rate of osmosis.

U.S. Pat. Nos. 5,180,475 and 5,240,585 also disclose changing the rate of electroosmotic flow by connecting different voltages to the inlet and outlet ends of the capillary tube to create a difference in potential, and then varying the two voltages.

SUMMARY OF THE INVENTION

The present invention relates to a process for monitoring electroosmotic flow directly by the application of an alternating voltage (AV) field centered upon an offset constant voltage (DV), which is applied as the separation voltage for capillary electrophoresis, and monitoring the resultant alternating current (AC) and direct current (DC) separately. This process is based on the transport or flux of ions in the diffuse layer near the inner wall of the capillary under the influence of the DV field. This flux of ions (Definition of current) will contribute to the total DC, whereas it will not add to the AC, and is a direct function of electroosmotic flow. Since this flux occurs in the presence of a DV field and not the AV field, but both resultant AC and DC respond to changes in the internal environment of the capillary (temperature, concentration, etc.), this presents a method to correlate current measurements to a function of electroosmotic flow. This is accomplished by realizing that the current is a function of the applied voltage and the internal environment of the capillary. To eliminate the applied voltage as a variable, it is divided by the resultant current leading to a measurement of impedance or apparent resistance of the system at a given frequency. By subtracting the DC impedance from the AC impedance, the resulting value is a direct measure of the ion flux in the diffuse layer (electroosmotic flow) normalized for the internal environmental variations of the capillary.

The apparatus for carrying out the present process provides for a constant voltage, an alternating voltage field and separate alternating and direct current monitoring.

The direct measurement of electroosmotic flow enables the concept of external voltage field flow control to be fully utilized. The flow measurement results can be fed back into the flow control system to either maintain a stable and constant flow, to create a variable flow, to stop flow or to reverse flow all in a dynamic manner.

The present monitoring system can be used in existing capillary electrophoresis (CE) systems to allow precise, real-time monitoring of electroosmotic flow. This enables the flow to be controlled through an electronic feedback loop to an external radial voltage flow control system, and allows precise and constant flow or flow programming which is presently unavailable in CE systems.

The present invention provides an improved system for monitoring electroosmotic flow during capillary electrophoresis by employing an alternating voltage field applied across the buffer-filled capillary in addition to the usual constant or direct voltage used in capillary electrophoresis, and monitoring the resultant AC and DC separately.

This invention provides an electroosmotic flow-monitoring system which only requires an additional alternating voltage source and an alternating current-detecting electronics in association with conventional capillary electrophoresis equipment, and which can be combined with the electronic control of electroosmotic flow to provide an apparatus for the programming of electroosmotic flow during an analytical analysis.

The present electrophoretic separation process and apparatus includes a capillary tube having a length, a cross-section, an inlet end and an outlet end. A first reservoir containing a solvent and, during injection, a solute is in fluid-flow communication with the inlet end of the capillary tube, and a second reservoir containing at least a solvent is in fluid flow communication with the outlet end of the capillary tube, the capillary thereby being filled at least with the solvent. A first power supply applies a DV separation potential between the first and second reservoirs and along the length of the capillary tube to thereby establish an electrophoretic flow of the solute therethrough. In addition to this constant direct voltage field, an alternating voltage field is applied, and the current due to this additional field is monitored. The relationship of the applied voltage divided by the resulting current defines the resistance across the capillary. The resistance across the capillary, as measured by the alternating voltage/alternating current, will appear to be greater than the resistance measured by the constant voltage/direct current. This is due to the flux ions within the diffuse layer caused by electroosmotic flow adding to the direct current measurement, but not to the alternating current measurement. This change in resulting current is a direct function of electroosmotic flow and can be measured to provide a real time monitoring of the electrophoretic flow velocity.

DESCRIPTION OF PREFERRED EMBODIMENT

Figure 1:
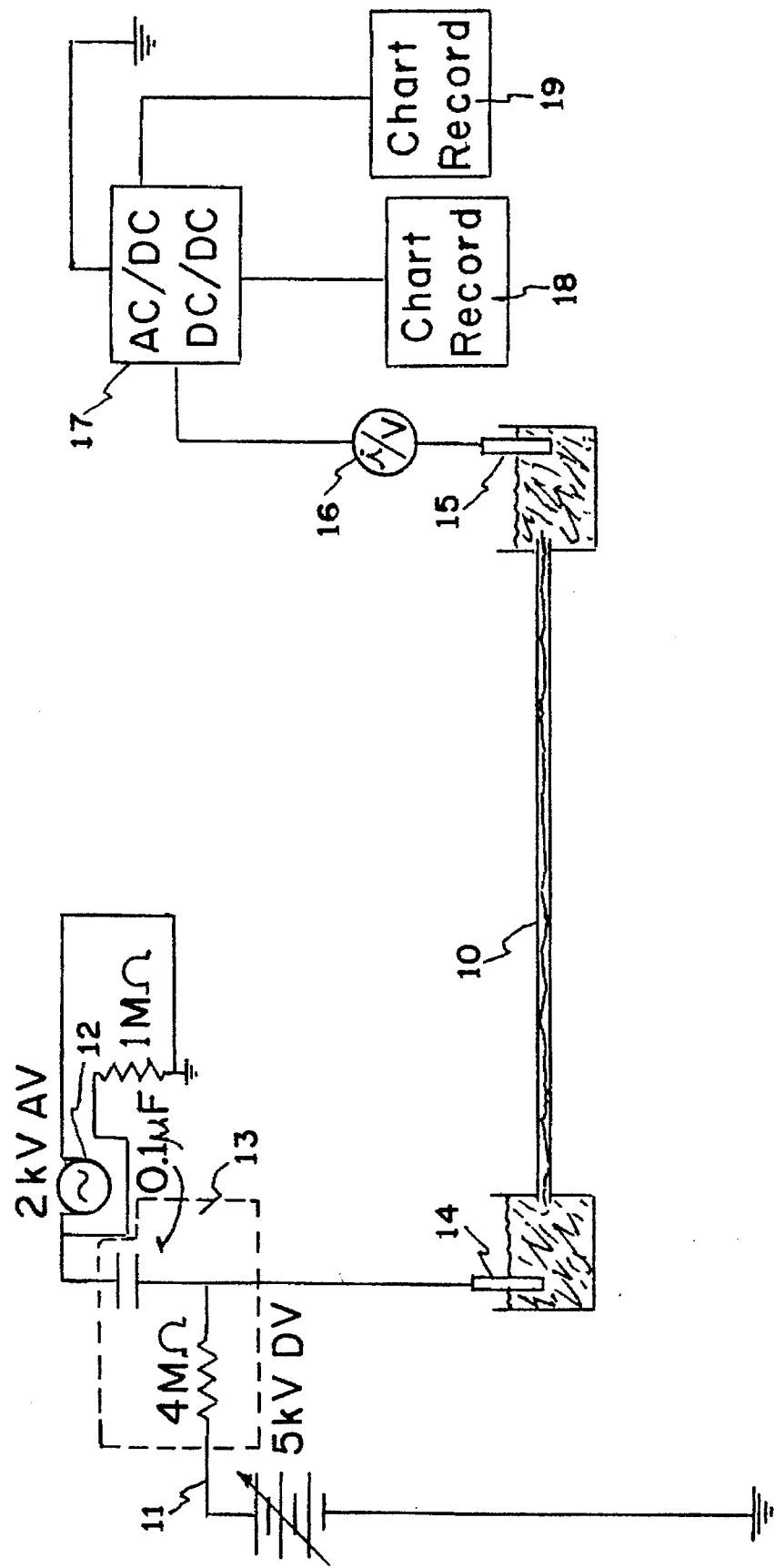
FIG. 1 is a schematic drawing of a capillary zone electrophoresis apparatus containing the electronics required to apply an alternating voltage field and to detect the resultant current.

The invention employs capillary electrophoresis to correlate current measurements across the capillary with electroosmotic flow as measured by the ion flux within the diffuse layer. This is accomplished as illustrated by FIG. 1, by applying an alternating voltage field across a capillary tube 10, such as a 20 μm i.d., 140 μm o.d. and 60 cm long fused silica capillary (Polymicro, Phoenix, Ariz.), while applying a constant voltage field between anode 14 and cathode 15 using a reversible high voltage power supply 11 (Spellman, Plainview, N.Y.) held at 5 kV. The alternating voltage field such as 300 V (p-p) at 7 Hz., may be applied through a 100 times amplifier 12 built in-house with a high voltage power supply (Bertan Associates, Hicksville, N.Y.) used as the power source. These voltages are applied according to the schematic shown in FIG. 1 through an isolation tee 13 consisting of a 0.1 μF capacitator (10 kV) (Newark Electronics, Chicago, Ill.) and a 4 MΩ resistor (Newark Electronics, Chicago, Ill.).

The capillary 10 is liquid-filled with a supporting electrolyte and terminates just after passing through a Linear 200 absorption detector (Linear Instruments, Reno, Nebr.). The cathode 15 is attached to a current-to-voltage converter and amplifier 16 (Keithly Instruments, Inc., Cleveland, Ohio). The output signal from the converter 16 is divided into the alternating and direct component by a converting rectifier 17. The signal for each component is output to a separate channel on a two-pen chart recorder 18 and 19 (Fisher Recordall, series 5000, Springfield, N.J.). In addition to the apparatus shown in FIG. 1, an applied radial voltage was utilized to affect changes in the electroosmotic flow.

The system tested used two plexiglas interlock boxes to house the high potential field portions of the capillary 10. The high potential lead for the separation potential and the injection end of the polyimide-coated fused silica capillary 10 were enclosed in the first box. The second box contained the portion of the capillary 10 for the applied radial voltage.

An ultraviolet detector (Linear 200, Reno, Nebr.) was installed on-line, i.e., approximately 6 cm from one end of the capillary 10, a 2 mm section of the polyimide coating was removed by heat to provide a UV-detection window. Data was collected at a wavelength of 200 nm. The current was detected as described above.

Solutions were made from $NaH_2PO_4$ (Sigma Chemical, St. Louis, Mo.) and adjusted to the desired pH with NaOH (Baker Chemical, Phillipsburg, N.J.). Phenol (Sigma Chemical Co.) was used as a probe molecule.

Figure 2:
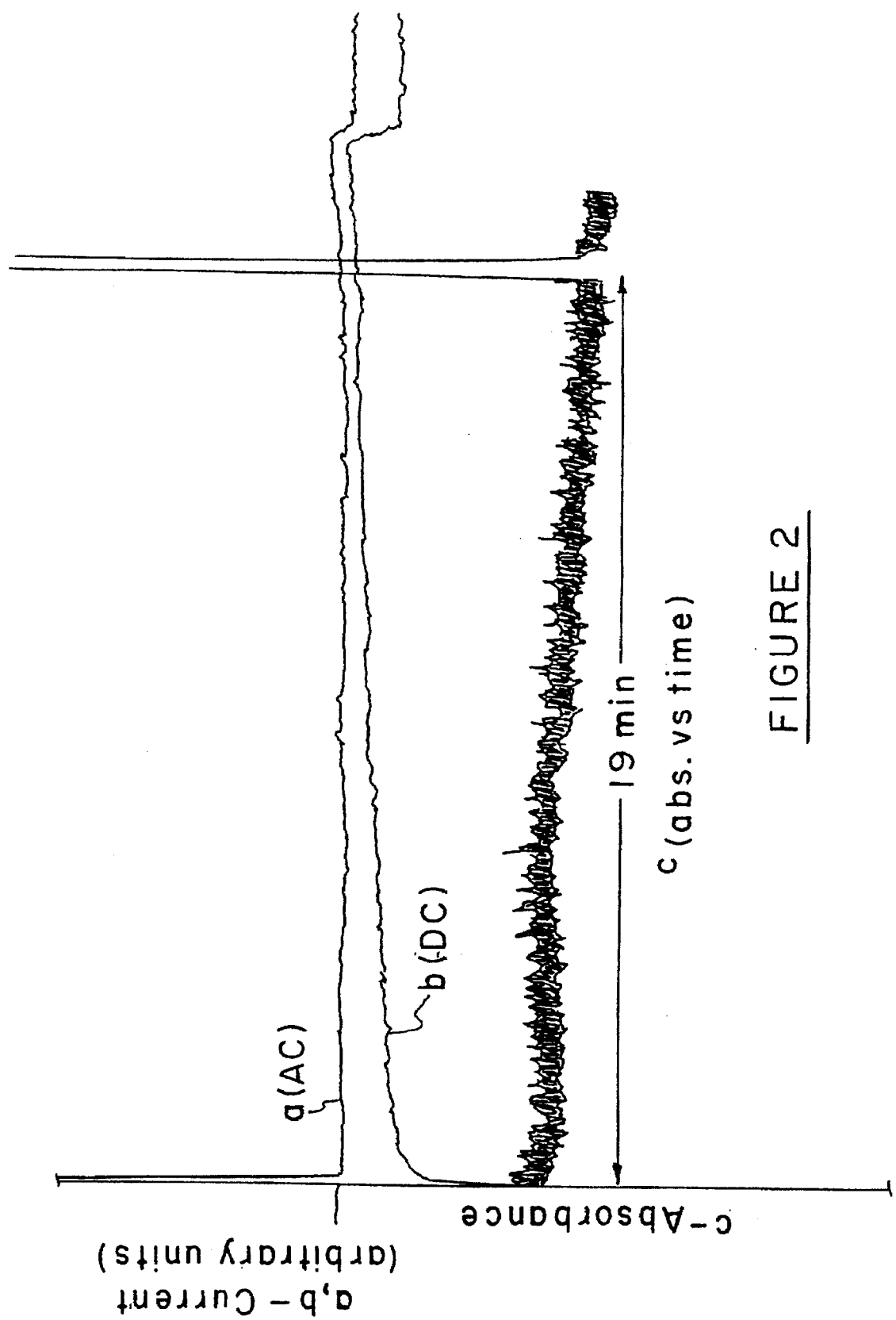
FIG. 2 is a graph plotting a), alternating current b), direct current and c) absorption vs time, according to the present process, absorption vs time determining the migration time for a neutral solute (phenol); Current measurements determine the average current during the migration.
Figure 3:
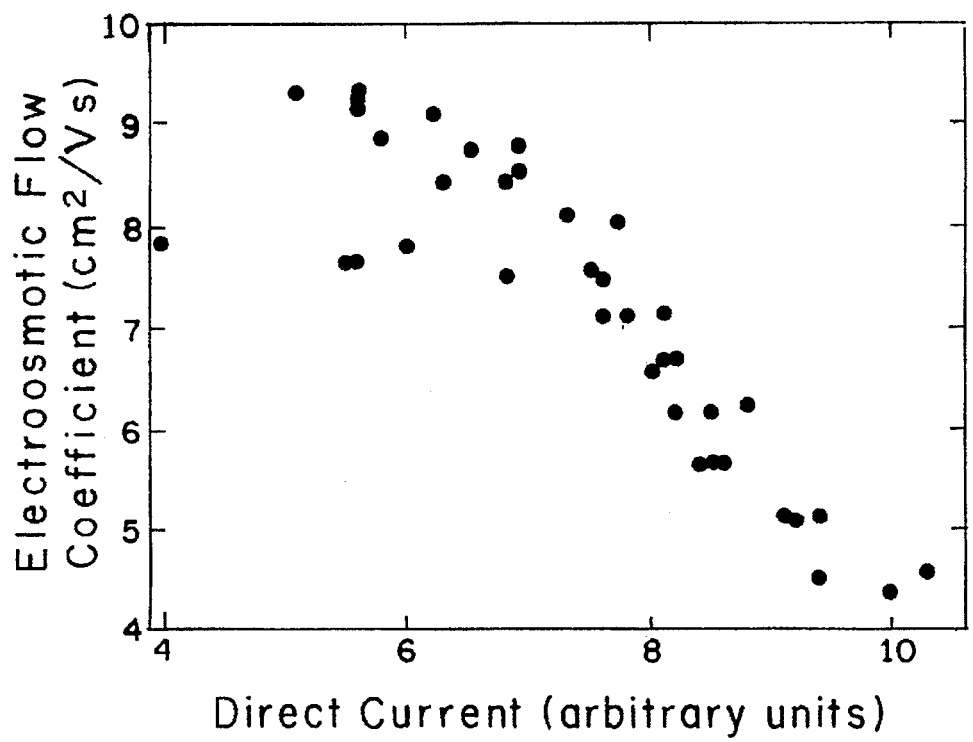
FIG. 3 is a graph plotting electroosmotic flow rate (given as a coefficient) vs direct current during the present process.
Figure 4:
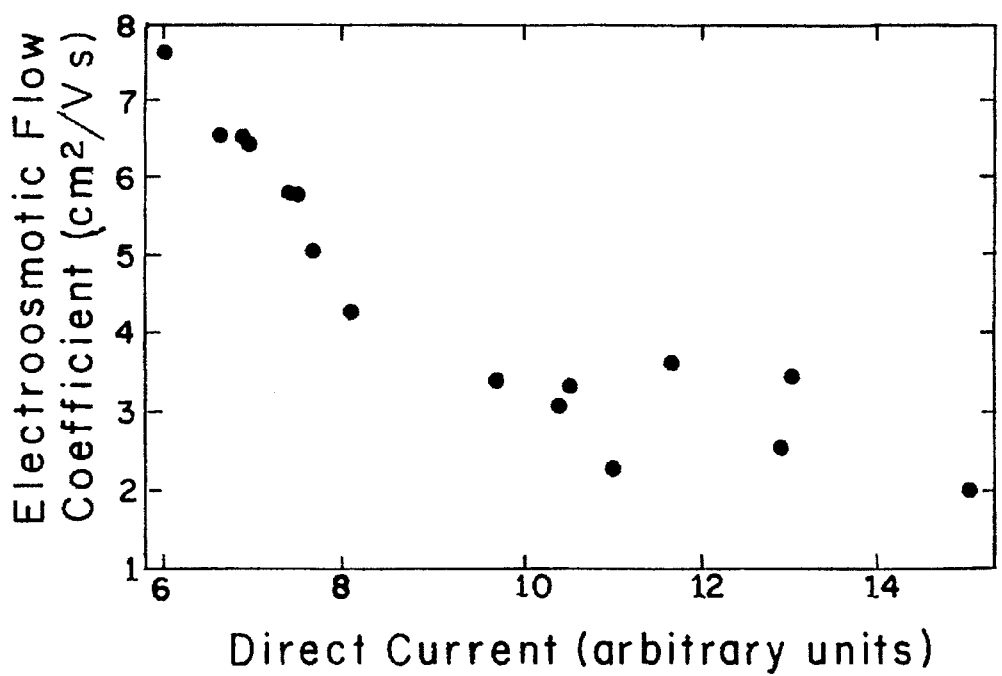
FIG. 4 is a graph showing variation in electroosmotic flow coefficient vs direct current during the present process.

Current across a capillary electrophoresis capillary 10 may be thought of as arising from two sources: ion mobility and differential ion flux due to transport of ions in the diffuse layer caused by electroosmotic flow. Higher flow rates should increase the ion flux from the transport within the diffuse layer, but should not affect the current due to ion mobility. This fact is exploited by simply measuring the current across the capillary under constant voltage conditions. If the internal properties of the capillary, such as the temperature and concentration, are held constant, a relationship between flow and current is observed. However, any fluctuations in applied voltage, temperature or concentration will cause an effect on the current and will negate any direct correlation. An example of this type of data is shown in FIGS. 3 and 4. A method of normalizing or "accounting for" changes in the temperature and concentration independent of electroosmotic flow is to measure the current under alternating voltage conditions. The alternating current is due to ion mobility only. Ion mobility reflects changes in the concentration and temperature. The present capillary electrophoresis apparatus provides first a direct current to the applied constant voltage that is a function of flow, concentration and temperature, and second an alternating current due to the alternating voltage that is a function of concentration and temperature only. By normalizing the direct current measurement with the alternating current values, the resulting measurement is a function flow only. This may be formalized by stating that the apparent resistance, $R_{DC}$, for the constant voltage measurement, will appear to be slightly smaller than the apparent resistance, $R_{AC}$, for the alternating voltage measurements due to the additional ion flux from the ion transport in the diffuse layer. This of course is described by Ohms law V/i=R where the current for DC measurements is slightly higher than the AC measurement. It may be simply stated that the number of ions in the diffuse layer is a function of the surface charge of the capillary wall and the flux is directly due to electroosmotic flow velocity, which is a function of the electroosmotic flow coefficient. A clear example of the conductivity of the solution increasing is illustrated by FIG. 2. The AC (a) is relatively constant whereas the DC (b) rises, reflecting an increased conductivity over time.

Figure 5:
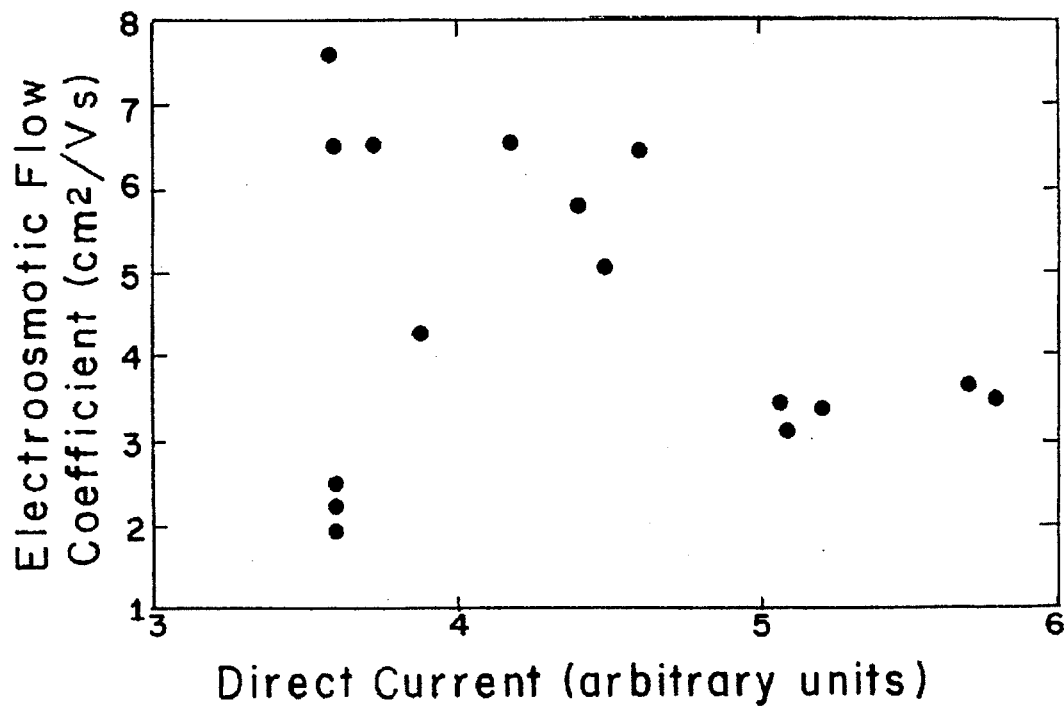
FIG. 5 is a graph showing variation in electroosmotic flow coefficient vs alternating current during the present process.
Figure 6:
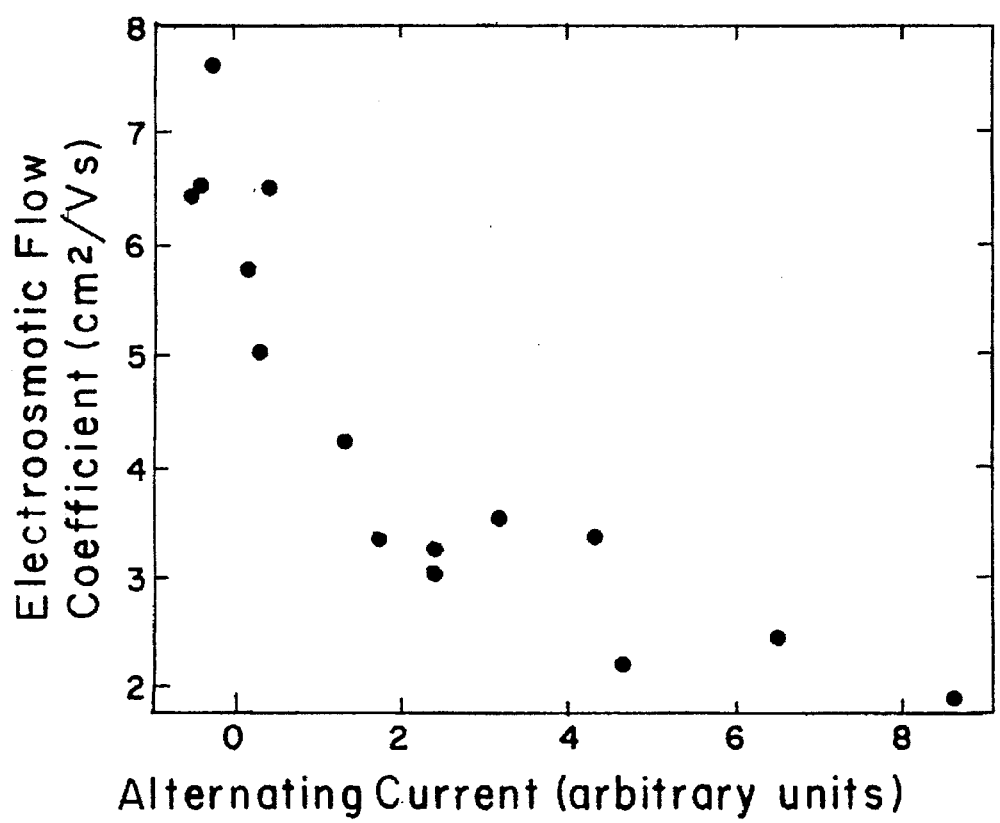
FIG. 6 is a graph showing variation in the resulting signal when subtracting the alternating current from the direct current plotted vs electroosmotic flow coefficient.

On the basis of this relationship, preliminary data were taken for direct current measurements, alternating current measurement and the result of subtracting the alternating current values from the direct current values (without accounting for applied voltages for each case). FIGS. 3 and 4 are the electroosmotic flow as measured by the neutral marker method plotted vs the average direct current across the capillary during each run. Each of these data sets show a slight, but not substantial, trend. FIG. 5 is a similar plot of electroosmotic flow as compared to the alternating current averaged over each run. This reflects the expected result, predicted by theory, that the AC is independent of electroosmotic flow and the large scatter, with no apparent trend, certainly agrees with this lack of a relationship. Finally, taking the average alternating current and subtracting it from the average direct current from each run results in the relationship plotted in FIG. 6. This is the direct current normalized for concentration and temperature fluctuations reflected in the alternating current measurements, and clearly shows a relationship between normalized current and electroosmotic flow, which provides a signal that is directly and reproducibly related to the magnitude of the electroosmotic flow. This ability to measure a signal proportional to electroosmotic flow can be used to electronically determine a voltage to be applied externally to alter the flow in a controllable fashion to either maintain a stable and constant flow, to create a variable flow, to stop flow or to reverse flow, all in a dynamic manner.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. Electrophoretic separation apparatus comprising:

capillary tube means having a length, a cross-section, an inlet end and an outlet end;

a first reservoir for containing a solvent and, upon injection, a solute, in fluid communication with said inlet end;

a second reservoir for containing at least a solvent, in fluid flow communication with said outlet end, said capillary tube thereby being filled with at least said solvent;

first power supply means for applying a direct voltage separation potential between said reservoirs and a flow of direct current along the length of said capillary tube to establish an electrophoretic flow of a said solute therethrough;

second power supply means for applying an alternating voltage to said first reservoir and producing a flow of alternating current along the length of said capillary tube to establish an alternating voltage field;

means for measuring the impedance to the direct and alternating currents produced across the capillary tube by the direct and alternating voltages, and means for calculating the difference between the AC impedance and the DC impedance to provide a direct measure of the electroosmotic flow, normalized for the internal environmental variations of the capillary.

2. A process for real-time monitoring of rate of electroosmotic flow of a solution from one reservoir to another connected by a capillary tube comprising the steps of:

(a) filling said reservoirs and said capillary tube with a liquid solvent;

(b) dissolving a solute in one of said reservoirs;

(c) applying a direct voltage separation potential between said reservoirs to establish a direct current and an electrophoretic flow of solute through said capillary tube;

(d) applying an alternating voltage to said first reservoir to produce an alternating current through said capillary tube and establish an alternating voltage, and (e) measuring the difference between the impedance to the direct and alternating currents produced across the capillary tube by the direct and alternating voltages, as a direct measure of the electroosmotic flow.

* * * * *